(12) United States Patent
Wei (10) Patent No.: US 10,330,492 B2
(45) Date of Patent: Jun. 25, 2019

(54) HUMAN ACTIVITY ENERGY CONSUMPTION MEASURING METHOD AND ENERGY CONSUMPTION MEASURING SYSTEM

(71) Applicant: BOE TECHNOLOGY GROUP CO., LTD., Beijing (CN)

(72) Inventor: Qiang Wei, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 422 days.

(21) Appl. No.: 14/443,790

(22) PCT Filed: Nov. 20, 2014

(86) PCT No.: PCT/CN2014/091780
§ 371 (c)(1),
(2) Date: May 19, 2015

(87) PCT Pub. No.: WO2015/196716
PCT Pub. Date: Dec. 30, 2015

(65) Prior Publication Data
US 2016/0273938 A1  Sep. 22, 2016

(30) Foreign Application Priority Data

Jun. 25, 2014  (CN) .......................... 2014 1 0289555

(51) Int. Cl.
*A61B 5/00* (2006.01)
*A61B 5/11* (2006.01)
(Continued)

(52) U.S. Cl.
CPC .......... *G01C 22/006* (2013.01); *A61B 5/1118* (2013.01); *A61B 5/4866* (2013.01);
(Continued)

(58) Field of Classification Search
None
See application file for complete search history.

(56) References Cited

U.S. PATENT DOCUMENTS

2006/0100817 A1    5/2006   You et al.
2007/0051369 A1*   3/2007   Choi .................. A61B 5/02438
                                              128/204.21
(Continued)

FOREIGN PATENT DOCUMENTS

CN       1723848 A    1/2006
CN     101061949 A   10/2007
(Continued)

OTHER PUBLICATIONS

International Search Report dated Apr. 16, 2015 issued in International Application No. PCT/CN2014/091780 along with the English translation of the Written Opinion.
(Continued)

*Primary Examiner* — J. H. Hur
(74) *Attorney, Agent, or Firm* — Nath, Goldberg & Meyer; Joshua B. Goldberg (57) ABSTRACT

The present invention provides an energy consumption measuring method and an energy consumption measuring system. According to the energy consumption measuring method and energy consumption measuring system provided by the present invention, by processing motion data of a user to acquire a corresponding motion feature vector of the user within a time period and comparing the acquired motion feature vector with a standard motion feature vector in a database, the energy consumption within this time period is acquired.

12 Claims, 2 Drawing Sheets

(51) Int. Cl.
*A63B 24/00* (2006.01)
*G01C 22/00* (2006.01)
*G06F 17/18* (2006.01)
*G06F 16/903* (2019.01)

(52) U.S. Cl.
CPC .... *A63B 24/0075* (2013.01); *G06F 16/90335* (2019.01); *G06F 17/18* (2013.01); *A61B 5/681* (2013.01); *A61B 2562/0219* (2013.01); *Y02D 10/45* (2018.01)

(56) References Cited

U.S. PATENT DOCUMENTS

| | | | |
|---|---|---|---|
| 2008/0204225 A1* | 8/2008 | Kitchen | A63B 21/072 340/539.22 |
| 2010/0105525 A1 | 4/2010 | Thukral et al. | |
| 2010/0292050 A1* | 11/2010 | DiBenedetto | A63B 24/0062 482/9 |
| 2011/0257496 A1* | 10/2011 | Terashima | A61B 5/4839 600/347 |
| 2011/0288784 A1* | 11/2011 | Jangle | A61B 5/1118 702/19 |
| 2013/0132319 A1* | 5/2013 | Landers | G06N 5/02 706/46 |
| 2015/0081061 A1* | 3/2015 | Aibara | A61B 5/1122 700/91 |

FOREIGN PATENT DOCUMENTS

| | | |
|---|---|---|
| CN | 101518442 A | 9/2009 |
| CN | 102657517 A | 9/2012 |
| CN | 102727185 A | 10/2012 |
| CN | 103181767 A | 7/2013 |
| CN | 103699795 A | 4/2014 |
| CN | 104111978 A | 10/2014 |
| JP | 2008173251 A | 7/2008 |

OTHER PUBLICATIONS

Wang Jiqin, "Research of the Moving Target Detection Algorithm Based on Global Motion Compensation", Dec. 12, 2012.
Office Action dated Nov. 4, 2016 issued in corresponding Chinese Application No. 201410289555.2.
European search report dated Jan. 17, 2018 for corresponding application No. 14861160.1.

* cited by examiner

HUMAN ACTIVITY ENERGY CONSUMPTION MEASURING METHOD AND ENERGY CONSUMPTION MEASURING SYSTEM

FIELD OF THE INVENTION

The present invention belongs to the field of energy consumption measurement technology, and particularly to an energy consumption measuring method and an energy consumption measuring system.

BACKGROUND OF THE INVENTION

A conventional pedometer measures the vibrations from human walking by a vibration sensor or an acceleration sensor, processes the measured data signal according to the stable frequency and velocity during walking of the human body and thus calculates the actual number of walking steps. As only the walking mode is taken into consideration, such a device can merely record the amounts of walking activity and the energy consumption therefrom, but cannot accurately measure and record other activities.

Many novel activity measurement devices may measure all-day motion and sleep conditions. Compared with the conventional pedometers merely for measuring the number of steps, these novel devices provide a feasible implementation way to accurately measure the activity of the human body and related fat expenditure in one day. Some researchers consider that measuring oxygen intake is the best way to measure the daily motion intensity. The motion intensity may be inferred according to the oxygen intake during quantified motion and rest, so it is required to establish a great number of calculation relations between the energy consumption and the oxygen intake.

However, for some anaerobic exercises (for example, swimming and weightlifting), the oxygen intake cannot actually reflect the activity and the energy consumed by the human body. Meanwhile, as a device for measuring the oxygen intake has low precision, there is a large measurement error.

In addition, although there are many kinds of physical sports in the real life, the types of physical sports usually done by a person are limited, so that the energy consumption is mainly concentrated in several limited motion forms. The complicated calculation relations between the energy consumption and the oxygen intake are time-consuming, labor-consuming, and low in use frequency. Therefore, it is necessary to provide an energy consumption measuring method and an energy consumption measuring system, which are more accurate in calculation, more flexible in setup and easier to use.

SUMMARY OF THE INVENTION

In view of the problems in the prior art, the technical solutions of the present invention are proposed.

According to one aspect of the present invention, an energy consumption measuring method is provided, including the following steps: acquiring motion data of a user within a time period; processing the acquired motion data to acquire a motion feature vector; comparing the acquired motion feature vector with a standard motion feature vector in a database so as to judge whether the motion mode of the user is matched with the database; acquiring an energy consumption value according to the data in the database if matching; and, allowing the user to create a customized motion model and input a corresponding energy consumption value if not matching.

According to an embodiment of the present invention, the motion data may be recorded and stored by an acceleration sensor and an angular velocity sensor.

According to an embodiment of the present invention, the step of acquiring a motion feature vector may include: partitioning the motion data into m data units in unit of certain time, each data unit contains n data points of each motion variable, wherein both m and n are natural numbers; for the m data units, calculating average values, variances and histogram slopes of the n data points of each motion variable in x-axis, y-axis and z-axis directions, respectively; performing Gaussian probability distribution calculation on the average values, variances and histogram slopes of the n data points of each motion variable of all the m data units in the x-axis, y-axis and z-axis directions to acquire discrete feature values and position feature values of a corresponding Gaussian distribution curve, and using a calculation result of least square fitting of the position feature values as a feature vector of the corresponding motion variable; and, using a set of the feature vectors of the motion variables as the motion feature vector of the corresponding data unit.

According to an embodiment of the present invention, the motion variables may include motion elements and user elements. The motion elements may include displacement, velocity, acceleration, height and time. The user elements may include age, gender, weight, height, vital capacity and body mass index.

According to an embodiment of the present invention, the comparison step may include: calculating a similarity of the acquired motion feature vector and the standard motion feature vector by a normalized Euclidean distance; comparing the acquired similarity with a set value; and, indicating matching when the absolute value of the similarity is less than the set value, and indicating not matching when the absolute value of the similarity is greater than or equal to the set value.

According to an embodiment of the present invention, the set value may be a discrete feature value of a Gaussian distribution curve of the standard motion feature vector.

According to an embodiment of the present invention, the database may include a user-customized motion model library and a cloud motion model library. The cloud motion model library may be configured to store a standard motion model and corresponding energy consumption thereof. The customized motion model library may be configured to store a motion feature vector which is not matched with the cloud motion model library, and store corresponding energy consumption input by the user.

According to another aspect of the present invention, an energy consumption measuring system is provided, including: a motion data acquisition unit, configured to acquire motion data of a user within a time period; a motion data processing unit, configured to process the acquired motion data to acquire a motion feature vector; and, a comparison unit, configured to compare the acquired motion feature vector with a standard motion feature vector in a database so as to judge whether the motion mode of the user is matched with the database, acquire an energy consumption value according to the data in the database if matching, and allow the user to create a customized motion model and input a corresponding energy consumption value if not matching.

According to an embodiment of the present invention, the motion data acquisition unit may include an acceleration sensor and an angular velocity sensor for recording and storing the motion data.

According to an embodiment of the present invention, the motion data processing unit may include: a data partition subunit, configured to partition the motion data into m data units in unit of certain time, each data unit contains n data points of each motion variable, wherein both m and n are natural numbers; a component calculation subunit, configured to, for the m data units, calculate average values, variances and histogram slopes of the n data points of each motion variable in x-axis, y-axis and z-axis directions, respectively; a discretizing and fitting subunit, configured to perform Gaussian probability distribution calculation on the average values, variances and histogram slopes of the n data points of each motion variable of all the m data units in the x-axis, y-axis and z-axis directions to acquire discrete feature values and position feature values of a corresponding Gaussian distribution curve, and use a calculation result of least square fitting of the position feature values as a feature vector of the corresponding motion variable; and, a motion feature vector generation subunit, configured to use a set of the feature vectors of the motion variables as a motion feature vector of the corresponding data unit.

According to an embodiment of the present invention, the database may include a user-customized motion model library and a cloud motion model library. The cloud motion model library may be configured to store a standard motion model and corresponding energy consumption thereof. The customized motion model library may be configured to store a motion feature vector which is not matched with the cloud motion model library, and store corresponding energy consumption input by the user.

According to an embodiment of the present invention, the energy consumption measuring system may further include a data transceiver unit, configured to request motion model data from the database, and receive or transmit the motion model data.

According to an embodiment of the present invention, the energy consumption measuring system may further include an energy consumption acquisition unit. When the motion mode of the user is matched with the database, the energy consumption acquisition unit may acquire the corresponding energy consumption according to the standard motion feature vector in the database. When the motion mode of the user is not matched with the database, the energy consumption acquisition unit may acquire energy consumption input by the user.

According to an embodiment of the present invention, the energy consumption measuring system may further include a display unit configured to display the energy consumption acquired by the energy consumption acquisition unit.

According to the energy consumption measuring method and energy consumption measuring system provided by the present invention, the activity content of a user may be monitored all the day to acquire corresponding motion data, and the motion data within a particular time period may be processed to acquire a motion feature vector of this time period. Matching between the acquired motion feature vector and the database is performed. If the matching is successful, a corresponding standard motion feature vector and corresponding energy consumption are acquired; and, if the matching is failed, the user is allowed to customize a motion model and input corresponding energy consumption. Accordingly, the energy consumption measuring method and the energy consumption measuring system are provided, which are more accurate in calculation, more flexible in setup and easier to use.

DETAILED DESCRIPTION OF THE INVENTION

To make those skilled in the art better understand the technical solutions of the present invention, the present invention will be further described as below in details in conjunction with the accompanying drawings and specific embodiments.

Figure 1:
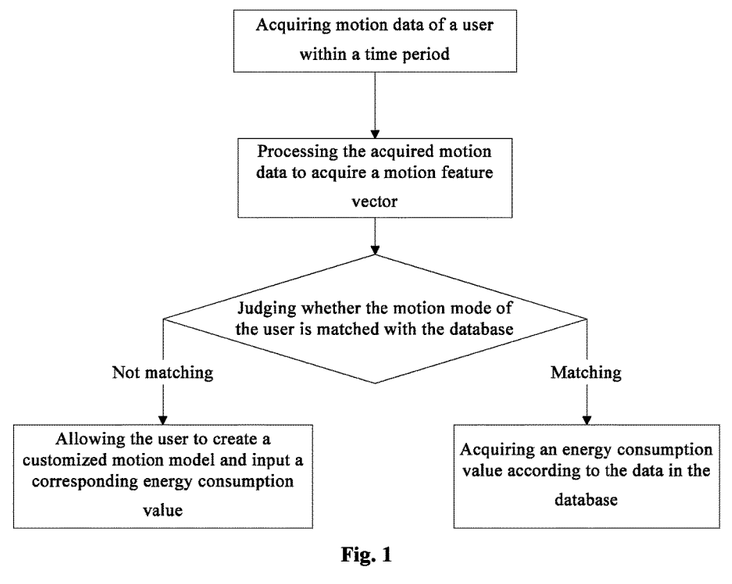
FIG. 1 is a flowchart of an energy consumption measuring method according to an embodiment of the present invention.

FIG. 1 is a flowchart of an energy consumption measuring method according to an embodiment of the present invention.

As shown in FIG. 1, the energy consumption measuring method according to the embodiment of the present invention may include the following steps: acquiring motion data of a user within a time period; processing the acquired motion data to acquire a motion feature vector; comparing the acquired motion feature vector with a standard motion feature vector in a database so as to judge whether a motion mode of the user is matched with the database; acquiring an energy consumption value according to the data in the database if matching; and, allowing the user to create a customized motion model and input a corresponding energy consumption value if not matching.

Specifically, the motion data may be recorded and stored by an acceleration sensor and an angular velocity sensor.

Daily motions of a user, such as walking, running, climbing the stairs, going down the stairs, climbing mountains, skipping a rope, swimming, playing badminton, playing basketball and so on, are accompanied with particular motion trajectories. For example, as for playing badminton, since motions such as frequently waving arms, fast running, sudden stopping and jumping have particular information about displacement s, velocity v, acceleration a, height h and time t, the information may be recorded by an acceleration sensor and an angular velocity sensor (gyroscope), in order to form the motion data corresponding to the badminton motion. By calculating and processing the motion data within a particular time period, a motion feature vector of this time period may be acquired.

The motion feature vector includes motion variables in multiple dimensions. The motion variables may include motion elements and user elements. The motion elements may include displacement s, velocity v, acceleration a, height h, time t and other information. The user elements may include age, gender, weight, height, vital capacity, body mass index and other information. The dimension of the variables included in the motion feature vector may be properly adjusted according to the form of motion.

For example, as for a jumping action during playing badminton, the motion feature vector model may be expressed as $V_T$:

$$V_T = \begin{bmatrix} s_T \\ v_T \\ a_T \\ h_T \\ t_T \\ age_T \\ gender_T \\ weight_T \\ height_T \\ vc_T \\ BMI_T \end{bmatrix} \quad \text{Formula 1}$$

wherein $s_T$, $v_T$, $a_T$, $h_T$ and $t_T$ are one-dimensional arrays formed by n samples acquired within a motion time period, for example:

$$s_T = [s_0, s_1, s_2, s_3, \ldots, s_{n-1}] \quad \text{Formula 2}$$

The one-dimensional array $s_T$ includes components $s_x$, $s_y$ and $s_z$ in three motion directions, i.e., x-axis, y-axis and z-axis:

$$s_x = [s_{x0}, s_{x1}, \ldots, s_{xn-1}]$$
$$s_y = [s_{y0}, s_{y1}, \ldots, s_{yn-1}]$$
$$s_z = [s_{z0}, s_{z1}, \ldots, s_{zn-1}] \quad \text{Formula 3}$$

The $age_T$, $gender_T$, $weight_T$, $height_T$, $vc_T$ and $BMI_T$ in the $V_T$ denote information about age, gender, weight, height, vital capacity and body mass index of the user respectively.

By acquiring lots of vector data of the motion feature vector of a certain motion, discretizing the vector data in unit of certain time, and clustering lots of discretized vector variable data, so that the vector data having the same features are gathered within a certain region of a feature space to form a standard motion feature vector of this motion. As the motion feature vectors of different motions differ from one another, the motion feature vectors of different types of motions will be distributed within different regions of a feature space. Thus, a feature space corresponding to different motion types is formed. The motion data acquired by the user within a particular time is discretized and a motion feature vector corresponding to this time period may be acquired by a statistical method, in order to compare this motion feature vector with a motion feature vector in the feature space of different motion types.

The calculation method of acquiring the corresponding motion feature vector via the motion data within a particular time period will be described as below. As the motion feature vector has many variables, the following description is illustrated by taking the calculation of a displacement vector $\vec{s}$ (corresponding to the one-dimensional array $s_T$) of the displacement variable as an example, and the calculation methods of other variables are similar and will not be repeated one by one.

First, after the motion data of a certain motion within a time period is acquired by a sensor, the motion data is partitioned into m data units in unit of certain time, and each data unit contains n data points of the motion variable displacement s, wherein both m and n are natural numbers.

Then, for the m data units, average values, variances and histogram slopes of the n data points of the motion variable displacement s in x-axis, y-axis and z-axis directions are calculated:

$$\vec{s} = (\vec{s}_x, \vec{s}_y, \vec{s}_z) \quad \text{Formula 4}$$

In Formula 4, $\vec{s}_x$, $\vec{s}_y$ and $\vec{s}_z$ denote an average displacement value, a displacement variance and a histogram slope of the displacement vectors in the x-axis, y-axis and z-axis directions within a data unit, respectively, wherein $$\vec{s}_x = (\bar{s}_x, \delta_x, \vec{r}_x)$$
$$\vec{s}_y = (\bar{s}_y, \delta_y, \vec{r}_y)$$
$$\vec{s}_z = (\bar{s}_z, \delta_x, \vec{r}_z) \quad \text{Formula 5}$$

In Formula 5, $\bar{s}_x$, $\bar{s}_y$ and $\bar{s}_z$ denote the average values of the n data points of the displacement vector $\vec{s}$ in the x-axis, y-axis and z-axis directions within a data unit, respectively, $\delta_x$, $\delta_y$, and $\delta_x$ denote variances of the n data points of the displacement vector $\vec{s}$ in the x-axis, y-axis and z-axis directions within a data unit, respectively, and $\vec{r}_x$, $\vec{r}_y$, and $\vec{r}_z$ denote histogram slopes of the n data points of the displacement vector $\vec{s}$ in the x-axis, y-axis and z-axis directions within a data unit, respectively.

The calculation methods of $\bar{s}_x$, $\delta_x$, and $\vec{r}_x$ will be separately described as below by taking $\vec{s}_x$ as example.

$$\bar{s}_x = \frac{\sum_{i=0}^{n-1} s_{xi}}{n}, \quad \text{Formula 6}$$

$$\delta_x = \frac{\sum_{i=0}^{n-1} \sqrt{s_{xi}^2 - \bar{s}_x^2}}{\bar{s}_x}, \quad \text{Formula 7}$$

$$\vec{r}_x = [r_{x1}, r_{x2}, \ldots, r_{xn-1}], \text{ and} \quad \text{Formula 8}$$

$$r_{xi} = \frac{s_{xi} - s_{xi-1}}{s_{xi}}. \quad \text{Formula 9}$$

Then, Gaussian probability distribution calculation is performed on the average values, variances and histogram slopes of the n data points of the motion variable displacement s of all the m data units in the x-axis, y-axis and z-axis directions so as to acquire discrete feature values σ and position feature values μ of a corresponding Gaussian distribution curve, wherein the Gaussian function is as shown in Formula 10:

$$f(x) = \frac{1}{\sqrt{2\pi}\,\sigma} \exp\left(-\frac{(x-\mu)^2}{2\sigma^2}\right). \quad \text{Formula 10}$$

Least square fitting may be used to calculate μ.

The specific method is as follows: initially setting $\sigma_0$ and $\mu_0$, calculating and modifying σ and μ by an iteration approximating method for calculating the least value of a quadratic function, so as to minimize the sum of the distances from the Gaussian curve to the motion variable displacement s of all the m data units. In this case, a Gaussian vector (i.e., a position feature value) $\vec{\mu}_{opt}$ is a center vector of the motion variable of displacement s in the motion feature vector of this motion, and the discrete feature value $\sigma_{opt}$ is a set value for judging whether the data input by a user is this motion.

Central values of all motion variables of the motion feature vector are calculated, and a set of the feature vectors of all the motion variables is used as a motion feature vector V of the corresponding data unit.

According to the motion feature vector V of the user, the energy consumption of the user within a particular time period is acquired from a pre-established database of the motion feature vector V and energy consumption. Correspondence data of the motion feature vector V and energy consumption is stored in the database in advance.

The database is established on the basis of lots of test data. Generally, a correspondence table of motion feature vectors V and energy consumption is established by a calculation method using a general formula or by actual measurement of lots of data.

The establishment of the database by a calculation method using the general formula will be described as below.

For example, for running, the relationship between the consumed calorie and a motion feature vector V is as follows:

the running calorie(kcal)=weight(kg)×motion time (hour)×index K, wherein the index K=30÷velocity (min/400 m).

If the weight of a person is 60 kg, the long-distance running time is 1 h and the velocity is 3 min/400 m or 8 km/h, then the calorie consumed during running is equal to 60×1×30/3=600 kcal.

This calculation includes a part of calorie consumed by the improvement of a basal metabolic rate after motion, i.e., a part of calorie generated by the rise of body temperature after motion.

The formula calculation method is simple and does not need to acquire lots of data of a user for statistic analysis, but has few corresponding activity types and poor accuracy.

Another method for establishing a database is as follows: acquiring different motion data of many persons, measuring the energy consumption of each person during every motion by professional equipment, and recording the height, weight, BMI, gender and age of the corresponding person, so that a data table showing correspondence between the motion feature vector V and energy consumption is established when the person does different types of sports within a particular time period with respect to a particular motion feature vector V (the variables may include height, weight, BMI, gender, age, etc.).

For example, similarly, as for running, persons 50 KG, 60 KG and 70 KG in weight are allowed to run at the velocity of 3 min/400 m, 4 min/400 m and 5 min/400, respectively, and the energy consumption at different motion states (corresponding to different motion feature vectors V) are then measured, so that a relation table of energy consumption during running of the persons 50 KG, 60 KG and 70 KG in weight at the velocity of 3 min/400 m, 4 min/400 m and 5 min/400 m is established.

This database establishment method is accurate because data is actually measured with respect to persons having different height and weight at different motion states; however, its disadvantage is that the establishment of such a database containing the whole vector dimensional space is required to measure lots of actual data because the motion feature vector V has many dimensions, so that the establishment of the database is high in cost. However, considering that common user customized databases are allowed and all the user customized databases are shared, the cost of the establishment of databases may be greatly saved.

In the present invention, the motion data of the user is recorded by an acceleration sensor and an angular velocity sensor. It should be understood that the acceleration sensor and the angular velocity sensor may be disposed in intelligent bracelets, armlets, necklaces or other devices that the user wears. But, only according to the data such as displacement, velocity and acceleration recorded by the acceleration sensor, it is difficult to directly resolve a continuous action of a user into motion units of running, jumping or waving an arm, so it is required to calculate motion feature vectors of motion data in data units small enough and then compare the motion feature vector corresponding to each data unit with a standard motion feature vector in a database, so as to determine which motion is performed by the user in a certain data unit and thus acquire the energy consumption corresponding to the standard motion feature vector.

Specifically, the way of judging which motion is performed by a user in a certain data unit will be described as below. Preferably, comparing the motion feature vector with the standard motion feature vector utilizes a similarity of the acquired motion feature vector and the standard motion feature vector by a normalized Euclidean distance. When the absolute value of the similarity is less than the set value, it is indicated matching; and, when the absolute value of the similarity is greater than or equal to the set value, it is indicated not matching. Preferably, the set value may be a discrete feature value $\sigma_{opt}$ of a Gaussian distribution curve of the standard motion feature vector.

First, it is required to calculate a motion feature vector $V_T$ of a user within a certain data unit, wherein the calculation method is the same as above.

Then, by calculating a normalized Euclidean distance between the motion feature vector $V_T$ of the motion of the user within a particular time period and the standard motion feature vector V in the database, the similarity $d_u$ between $V_T$ and V is calculated. The specific calculation method is as shown in Formula 11:

$$d_u = \frac{V - V_T}{V_T} = \begin{bmatrix} \frac{\sqrt{s^2 - s_T^2}}{s_T} \\ \frac{\sqrt{v^2 - v_T^2}}{v_T} \\ \frac{\sqrt{a^2 - a_T^2}}{a_T} \\ \frac{\sqrt{h^2 - h_T^2}}{h_T} \\ \frac{\sqrt{t^2 - t_T^2}}{t_T} \\ \frac{\sqrt{age^2 - age_T^2}}{age_T} \\ \frac{\sqrt{gender^2 - gender_T^2}}{gender_T} \\ \frac{\sqrt{weight^2 - weight_T^2}}{weight_T} \\ \frac{\sqrt{height^2 - height_T^2}}{height_T} \\ \frac{\sqrt{vc^2 - vc_T^2}}{vc_T} \\ \frac{\sqrt{BMI^2 - BMI_T^2}}{BMI_T} \end{bmatrix}. \quad \text{Formula 11}$$

Whether the motion is matched with the motion feature vector in the database is determined by comparing the absolute value of the similarity with the discrete feature value $\sigma_{opt}$ of the Gaussian distribution curve of this type of motion stored in the database.

If the value of $\sigma_{opt}$ is smaller, it is indicated that the judgment criterion of the motion feature similarity is higher. Thus, the motion feature vector of the user is more approximate to the standard motion feature vector, and the accuracy of the calculation of energy consumption is higher. Conversely, if $\sigma_{opt}$ is larger, it is indicated that the accuracy of the calculation of energy consumption is lower.

However, it is not true that the smaller $\sigma_{opt}$ the better. When $\sigma_{opt}$ becomes smaller, the whole motion feature vector space is more discrete, and more feature vectors are required to train and fill the standard motion feature vector space.

When it is judged matching, the corresponding energy consumption is acquired from the database.

When it is judged not matching, the user is allowed to create a customized motion model library, and then input the corresponding energy consumption by the user.

In other words, the database may include a user-customized motion model library and a cloud motion model library. The cloud motion model library may be configured to store a standard motion model and corresponding energy consumption thereof. The customized motion model library may be configured to store a motion feature vector which is not matched with the cloud motion model library, and store corresponding energy consumption input by the user.

Specifically, the cloud motion model library allows different users to upload data of the customized motion model library so as to continuously expand and complete the cloud motion model library. When there are a great many users and a great many samples of effective individual calorie consumption data of the users are uploaded, it is possible to create a huge and accurate standard motion vector feature space, so that the accurate standard motion model and corresponding energy consumption data thereof are better provided for each user.

According to the technical solutions provided by the present invention, by acquiring motion data of a user within a time period, partitioning the motion data into a plurality of data units, calculating a motion feature vector V corresponding to each data unit and comparing the motion feature vector V corresponding to each data unit with a standard motion feature vector in a database, the motion of the user may be divided into different motion units and then the energy consumption thereof is calculated separately. For example, by partitioning the badminton motion data of a user within a time period into a plurality of data units, calculating a motion feature vector V corresponding to each data unit separately and comparing the motion feature vector V corresponding to each data unit with a standard motion feature vector in a database, the badminton motion of the user may be decomposed into different motion units such as running, jumping and waving an arm; then, the number and the motion time of each motion unit are counted, so that the energy consumption in the whole badminton motion is calculated. The energy consumption measuring method provided by the present invention is more accurate in calculation, more flexible in setup and easier to use.

Figure 2:
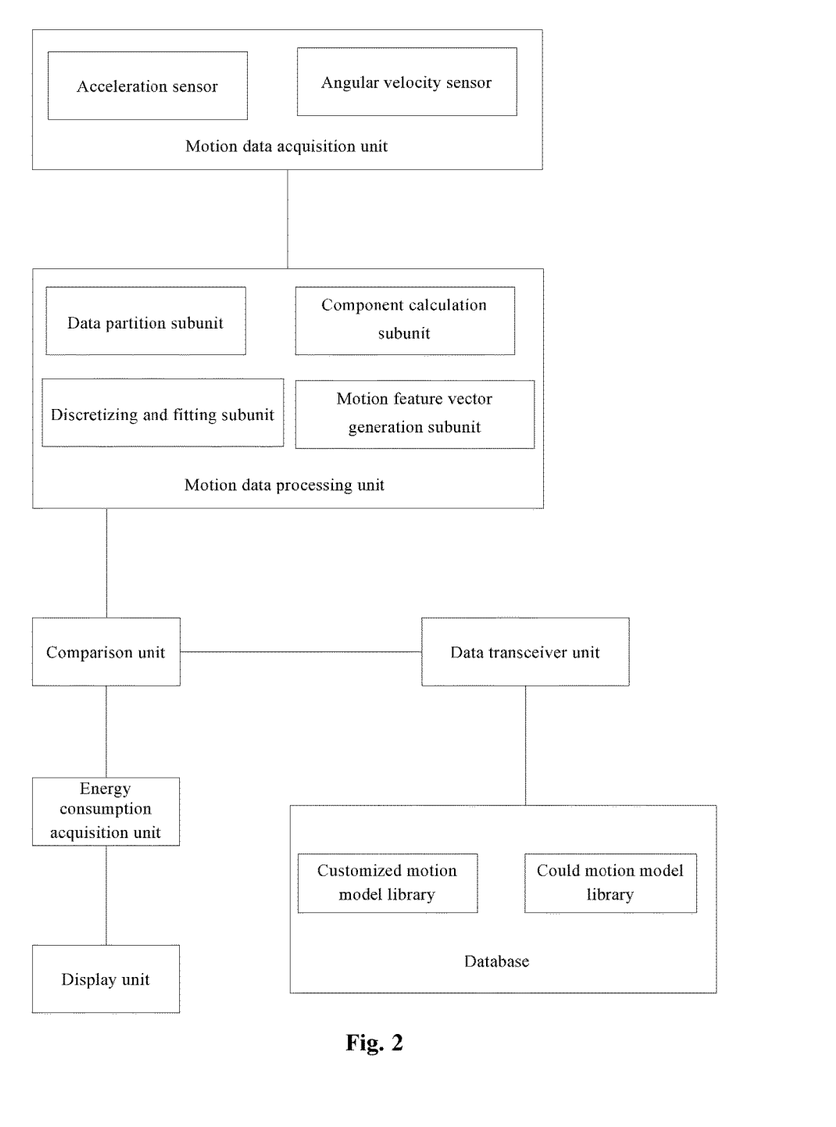
FIG. 2 is a composition diagram of an energy consumption measuring device according to an embodiment of the present invention.

FIG. 2 is a composition diagram of an energy consumption measuring device according to an embodiment of the present invention.

As shown in FIG. 2, the energy consumption measuring system according to the embodiment of the present invention may include: a motion data acquisition unit, configured to acquire motion data of a user within a period of time; a motion data processing unit, configured to process the acquired motion data to acquire a motion feature vector; and, a comparison unit, configured to compare the acquired motion feature vector with a standard motion feature vector in a database so as to judge whether the motion mode of the user is matched with the database, acquire an energy consumption value according to the data in the database if matching, and allow the user to create a customized motion model and input a corresponding energy consumption value if not matching.

Specifically, the comparison unit is configured to receive the motion feature vector calculated by the motion data processing unit and the standard motion feature vector data sent by a data transceiver unit, and calculate the similarity of the both by a normalized Euclidean distance. When the absolute value of the similarity is less than the set value, it is judged matching; and, when the absolute value of the similarity is greater than or equal to the set value, it is judged not matching.

The motion data acquisition unit may include an acceleration sensor and an angular velocity sensor for recording and storing the motion data. These sensors may be disposed in intelligent bracelets, armlets, necklaces or other devices that the user wears, for acquiring the motion data of the user all the day.

The motion data processing unit may include: a data partition subunit, configured to partition the motion data into m data units in unit of certain time, each data unit contains n data points of each motion variable, wherein both m and n are natural numbers; a component calculation subunit, configured to, for the m data units, calculate average values, variances and histogram slopes of the n data points of each motion variation in x-axis, y-axis and z-axis directions, respectively; a discretizing and fitting subunit, configured to perform Gaussian probability distribution calculation on the average values, variances and histogram slopes of the n data points of each motion variation of all the m data units in the x-axis, y-axis and z-axis directions to acquire discrete feature values and position feature values of a corresponding Gaussian distribution curve, and use a calculation result of least square fitting of the position feature values as a feature vector of the corresponding motion variable; and, a motion feature vector generation subunit, configured to use a set of the feature vectors of the motion variables as a motion feature vector of the corresponding data unit.

The energy consumption measuring system provided by the present invention may further include a data transceiver unit, configured to request motion model data from the database, and receive or transmit the motion model data. Specifically, the data transceiver unit includes a wireless network connection. A user uploads a customized motion model library or downloads the related data of a standard motion model library by the wireless network connection.

The energy consumption measuring system provided by the present invention may further include an energy consumption acquisition unit. When the motion mode of the user is matched with the database, the energy consumption acquisition unit may acquire the corresponding energy consumption according to the standard motion feature vector in the database. In the case of not matching, the energy consumption acquisition unit may acquire energy consumption input by the user.

The energy consumption measuring system provided by the present invention may further include a display unit configured to display the energy consumption acquired by the energy consumption acquisition unit. Specifically, the display unit may be a liquid crystal display screen or an OLED screen for displaying the energy consumption of the motion of the user.

It could be understood that the foregoing embodiments are exemplary implementations merely for describing the principle of the present invention, but the present invention is not limited thereto. A person of ordinary skill in the art may make various modifications and improvements without departing from the spirit and essence of the present invention, and these modifications and improvements are also consider as within the protection scope of the present invention.

The invention claimed is:

1. An energy consumption measuring method, comprising:
   acquiring motion data of a user within a time period;
   processing, by a motion data processing unit, the acquired motion data to acquire a motion feature vector;
   comparing the acquired motion feature vector with a standard motion feature vector in a database so as to judge whether a motion model of the user matches a motion model in the database;
   acquiring an energy consumption value according to the data in the database if matching; and
   allowing the user to create a customized motion model and input a corresponding energy consumption value if not matching,
   wherein the acquiring a motion feature vector comprises:
   partitioning, by a data partition subunit of the motion data processing unit, the motion data into m data units in unit of certain time, each data unit contains n data points of each of motion variables, wherein both m and n are natural numbers greater than or equal to two, the motion variables include displacement, velocity and acceleration, and the displacement, the velocity and the acceleration are acquired by an acceleration sensor and an angular velocity sensor;
   for the m data units, calculating, by a component calculation subunit of the motion data processing unit, average values, variances and histogram slopes of the n data points of each of the motion variables in x-axis, y-axis and z-axis directions, respectively;
   performing, by a discretizing and fitting subunit of the motion data processing unit, Gaussian probability distribution calculation on the average values, variances and histogram slopes of the n data points of each of the motion variables of all the m data units in the x-axis, y-axis and z-axis directions to acquire discrete feature values and position feature values of a corresponding Gaussian distribution curve, and using a calculation result of least square fitting of the position feature values as a feature vector of the corresponding motion variable; and
   using, by a motion feature vector generation subunit of the motion data processing unit, a set of the feature vectors of the motion variables as the motion feature vector of the corresponding data unit.

2. The energy consumption measuring method according to claim 1, wherein the motion data is recorded and stored by the acceleration sensor and the angular velocity sensor.

3. The energy consumption measuring method according to claim 1, wherein the motion variables comprise motion elements and user elements, the motion elements comprising the displacement, the velocity and the acceleration, and further height and time, the user elements comprising age, gender, weight, height, vital capacity and body mass index.

4. The energy consumption measuring method according to claim 1, wherein the comparing comprises:
   calculating a similarity of the acquired motion feature vector and the standard motion feature vector by a normalized Euclidean distance;
   comparing the acquired similarity with a set value; and
   indicating matching when the absolute value of the similarity is less than the set value, and indicating not matching when the absolute value of the similarity is greater than or equal to the set value.

5. The energy consumption measuring method according to claim 4, wherein the set value is a discrete feature value of a Gaussian distribution curve of the standard motion feature vector.

6. The energy consumption measuring method according to claim 1, wherein the database comprises a user-customized motion model library and a cloud motion model library,
   the cloud motion model library is configured to store a standard motion model and corresponding energy consumption thereof, and
   the customized motion model library is configured to store a motion feature vector which is not matched with the cloud motion model library, and store corresponding energy consumption input by the user.

7. An energy consumption measuring system, comprising:
   a motion data acquisition unit, configured to acquire motion data of a user within a time period;
   a motion data processing unit comprising an acceleration sensor and an angular velocity sensor, and configured to process the acquired motion data to acquire a motion feature vector; and
   a comparison unit, configured to compare the acquired motion feature vector with a standard motion feature vector in a database so as to judge whether a motion model of the user matches a motion model in the database, acquire an energy consumption value according to the data in the database if matching, and allow the user to create a customized motion model and input a corresponding energy consumption value if not matching,
   wherein the motion data processing unit comprises:
   a data partition subunit, configured to partition the motion data into m data units in unit of certain time, each data unit contains n data points of each of motion variables, wherein both m and n are natural numbers greater than or equal to two, the motion variables include displacement, velocity and acceleration, and the displacement, the velocity and the acceleration are acquired by the acceleration sensor and the angular velocity sensor;
   a component calculation subunit, configured to, for the m data units, calculate average values, variances and histogram slopes of the n data points of each of the motion variables in x-axis, y-axis and z-axis directions, respectively;
   a discretizing and fitting subunit, configured to perform Gaussian probability distribution calculation on the average values, variances and histogram slopes of the n data points of each of the motion variables of all the m data units in the x-axis, y-axis and z-axis directions to acquire discrete feature values and position feature values of a corresponding Gaussian distribution curve, and use a calculation result of least square fitting of the position feature values as a feature vector of the corresponding motion variable; and a motion feature vector generation subunit, configured to use a set of the feature vectors of the motion variables as the motion feature vector of the corresponding data unit.

8. The energy consumption measuring system according to claim 7, wherein the motion data is recorded and stored by the acceleration sensor and the angular velocity sensor.

9. The energy consumption measuring system according to claim 7, wherein the database comprises a user-customized motion model library and a cloud motion model library;

the cloud motion model library is configured to store a standard motion model and corresponding energy consumption thereof; and the customized motion model library is configured to store a motion feature vector which is not matched with the cloud motion model library, and store corresponding energy consumption input by the user.

10. The energy consumption measuring system according to claim 9, further comprising a data transceiver unit, configured to request motion model data from the database, and receive or transmit the motion model data.

11. The energy consumption measuring system according to claim 7, further comprising an energy consumption acquisition unit, wherein the energy consumption acquisition unit acquires the corresponding energy consumption according to the standard motion feature vector in the database when the motion model of the user matches the motion model in the database; and, the energy consumption acquisition unit acquires energy consumption input by the user in the case of not matching.

12. The energy consumption measuring system according to claim 11, further comprising a display unit configured to display the energy consumption acquired by the energy consumption acquisition unit.

* * * * *